(12) United States Patent
Bongrani et al.

(10) Patent No.: US 6,953,813 B1
(45) Date of Patent: Oct. 11, 2005

(54) 2-AMINOTETRALIN DERIVATIVES FOR THE THERAPY OF GLAUCOMA

(75) Inventors: Stefano Bongrani, Parma (IT); Roberta Razzetti, Parma (IT); Paolo Chiesi, Parma (IT)

(73) Assignee: Chiesi Farmaceutici S.p.A., Parma (IT)

(*) Notice: Subject to any disclaimer, the term of this patent is extended or adjusted under 35 U.S.C. 154(b) by 339 days.

(21) Appl. No.: 10/030,114

(22) PCT Filed: Jul. 26, 2000

(86) PCT No.: PCT/EP00/07184
§ 371 (c)(1),
(2), (4) Date: Apr. 26, 2002

(87) PCT Pub. No.: WO01/08667
PCT Pub. Date: Feb. 8, 2001

(30) Foreign Application Priority Data
Jul. 30, 1999 (IT) .......................... MI99A1713

(51) Int. Cl.$^7$ .......................... A01N 37/06; C07C 69/00
(52) U.S. Cl. .......................... 514/549; 560/139
(58) Field of Search .......................... 560/139; 514/549

(56) References Cited

U.S. PATENT DOCUMENTS 5,314,916 A * 5/1994 York et al.
6,013,678 A  1/2000 Chiesi et al.
6,103,760 A  8/2000 Chiesi et al.

FOREIGN PATENT DOCUMENTS

| EP | 0 009 702 | | 4/1980 |
| GB | 2 123 410 | | 2/1984 |
| GB | 2123410 | * | 2/1984 |
| WO | 96 29065 | | 9/1996 |
| WO | 96/29065 | * | 9/1996 |

OTHER PUBLICATIONS

Carmine Morisco et al.: "Hemodynamic effects of graded oral doses of a new dopaminergic analogue CHF 1035 in patients with congestive heart failure" Journal of the American College of Cardiology, no. Spec. Issue, p. 128A 1995.

* cited by examiner

*Primary Examiner*—Paul J. Killos
(74) *Attorney, Agent, or Firm*—Oblon, Spivak, McClelland, Maier & Neustadt, P.C.

(57) ABSTRACT

The use of racemic or optically active compounds represented by formula (I) and the salts thereof wherein R is H or $CH_3$ for the preparation of pharmaceutical compositions for the therapy of ophthalmic disorders.

17 Claims, 2 Drawing Sheets

Figure 1:
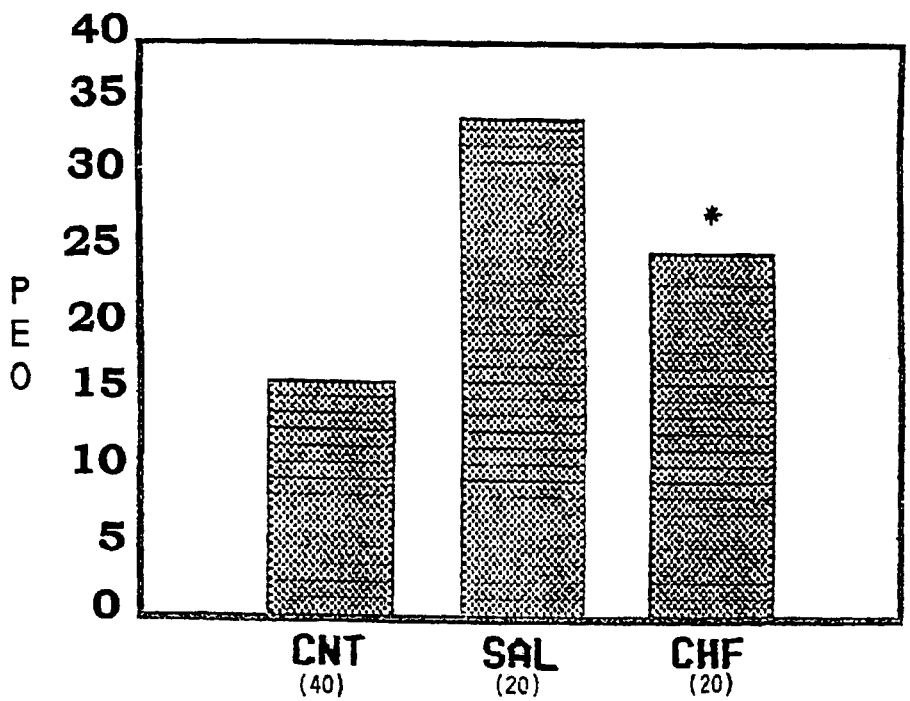

CNT = control values before lcarico idrico (the values of the two groups were combined).

SAL = animals treated with physiological saline.

CHF = animals treated with CHF 1035.

* Significant difference compared with the SAL group, p < 0.05 (two-way ANOVA).

CNT = control values before !carico idrico (the values of the two groups were combined).

SAL = animals treated with physiological saline.

CHF = animals treated with CHF 1035.

\* Significant difference compared with the SAL group, $p < 0.05$ (two-way ANOVA).

CNT = control values.

CHF = animals treated with CHF 1035.

\* Significant difference compared with the control group, $p < 0.05$ (two-way ANOVA).

2-AMINOTETRALIN DERIVATIVES FOR THE THERAPY OF GLAUCOMA

The present invention relates to the use of racemic or optically active compounds represented by formula I and the salts thereof

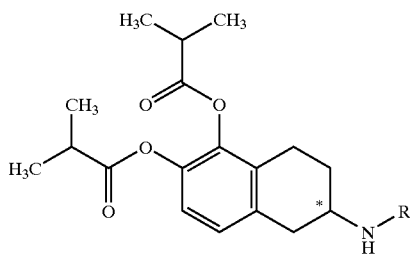

wherein R is H or $CH_3$,
for the preparation of pharmaceutical compositions for the therapy of ophtalmic disorders.

More particularly, the invention relates to the use of (±)-(R,S)-5,6-diisobutyroyloxy-2-methylamino-tetralin or its (−)-(S)-enantiomer in the preparation of ophthalmic formulations for the treatment of glaucoma.

Glaucoma is an ophthalmic disorder characterized by increased intraocular pressure which causes excavation and degeneration of the optic disc. Notwithstanding the therapeutical progresses attained, glaucoma, whose etiology has not yet been completely clarified, is one of the main causes of irreversible blindness.

Three types of glaucoma are known: primary, secondary and congenital glaucoma. Primary glaucoma is, in turn, classified in acute congestive or angle-closure glaucoma and simple chronic or open-angle glaucoma. The high intraocular pressure (IOP) is due to insufficient outflow of the aqueous humour from the eye anterior chamber. Therefore, the symptomatic therapy usually aims at decreasing the intraocular pressure, which can be attained via three mechanisms: i) increasing of the outflow of aqueous humor by use of direct parasympathomimetic or cholinesterase inhibitors; ii) dehydration of the eye bulbs by use of osmotic agents such as urea or mannitol; iii) reduction in the aqueous humor production by the ciliated epithelium: a number of medicaments, such as carbonic anhydrase inhibitors and β-blockers, act according to this mechanism.

The medicaments of the various classes cited above can be administered either alone or in combinations thereof.

Sympathomimetics have been widely used in the past, mainly in the treatment of open-angle glaucoma. These drugs act either through direct stimulation of adrenergic receptors or through release of catecholamines from the synaptic vesicles of the adrenergic nerve terminals. They differ both in their selectivity towards specific receptors and in the intensity of the adrenergic responses they give rise to. Depending on the type of receptors preferably involved, they can act either by promoting the outflow of aqueous humor or by decreasing its production. However, such drugs induce a number of side effects mainly connected with their aspecificity, therefore the use of such medicaments as adrenaline or its corresponding pro-drug dipivefrin is restricted to a combination therapy in patients in which β-blockers are contraindicated. In order to decrease the onset of side effects, research has been focused on drugs with higher selectivity, particularly towards pre-synaptic $\alpha_2$-adrenoceptors. $\alpha_2$-Agonists act both by promoting the outflow of aqueous humor and by decreasing its production. Two Clonidine analogues belonging to this pharmacological class, namely Brimonidine and Apraclonidine, have recently been introduced in therapy. The search for drugs for the treatment of glaucoma is also directed to dopamine analogues for their capability of stimulating α-adrenoceptors in addition to the dopaminergic ones. By virtue of this dual action, the decrease in intraocular pressure can take place through a plurality of mechanisms of action. In many experimental studies some $DA_2$-agonists were found particularly active; since they induce inhibition of catecholamines release in the eye, they can be functionally considered as indirectly acting β-blockers. Among dopaminergic medicaments, a number of aminotetralin derivatives have been the object of several studies and Patent applications.

Burke J et al. (J. Auton. Pharmac. 4, 185–192, 1984) report that 6,7-dihydroxy-2-aminotetralin and N,N-dimethyl-6,7-dihydroxy-2-aminotetralin, administered as ophthalmic drops, gives rise to eye hypotension in the rabbit. A subsequent study, carried out on the same experimental model by Thörig L et al. (Ophthalmic Res. 17, 362–372, 1985) showed that N,N-dimethyl-5,6-dihydroxy-2-aminotetralin (M-7) is active as well in reducing intraocular pressure but induces eye irritation already at a concentration of 0.1%. In a general way catechol derivatives are characterized by inherent stability problems which could adversely affect their successful pharmaceutical employment. Moreover the partition coefficient ($logP_{app}$) of 2-amminotetralins with the catechol group free is usually not optimal for ocular absorption (Schoenwald R D et al. J. Pharm. Sci. 72, 1266–1272, 1983 and J. Pharm. Sci. 67, 787–789, 1978).

U.S. Pat. No. 4,588,747 in the name of Synthelabo claims the use of N,N-propyl-6-hydroxy-formylamino-2 aminotetralins.

U.S. Pat. No. 4,657,925 in the name of Nelson R & D claims the use of variously substituted N-alkyl, N-arylalkyl-2-aminotetralins, acting on $DA_2$ receptors. More particularly, the use of 2-(N-propyl-N-2-thienylethylamino)-5-hydroxytetralin is claimed. Said derivative however, although exerting a long-lasting action, can also induce eye irritation.

U.S. Pat. No. 4,722,933, in the name of Alcon, claims the use of 5,6-acyloyloxy-1-hydroxy-2-aminotetralin derivatives lacking side effects on the cardiovascular system.

U.S. Pat. No. 5,382,596, EP 163458, U.S. Pat. No. 5,430,056, EP 627407, U.S. Pat. No. 5,140,040, U.S. Pat. No. 5,086,074 claim other aminotetralin derivatives utilizable in a number of pathologies, including glaucoma, which could benefit from a treatment based on dopaminergic medicaments. Said documents report no data supporting the effectiveness in the treatment of said disease.

None of these compounds has to-date been introduced in therapy. Therefore, a need exists for aminotetralin derivatives for the treatment of glaucoma which provides for potent control of elevated IOP without causing significant side effects, especially on the cardiovascular system. In particular, a need exists for derivatives with good local tolerability and topical bioavailability, soluble as well stable in aqueous medium and which do not show tolerance upon prolonged administration.

OBJECT OF THE INVENTION (±)-(R,S)-5,6-diisobutyryloxy-2-methylaminotetralin, (from now on referred to as CHF 1035), was first disclosed in GB 2,123,410 among a series of potentially antibronchospastic aminotetralin derivatives; afterwards the use of said compound in the treatment of cardiac disorders, particularly congestive heart failure, was claimed.

It has now been found that CHF 1035 can be effectively used in the treatment of glaucoma through the topical administration.

Studies carried out in normotensive rabbits as well as in rabbits with water-increased IOP showed that CHF 1035 in the form of ophthalmic drops significantly decreases, after single administration, the intraocular pressure.

As regards to the study in normotensive rabbits, advantageously, compared to brimonidine, no significant IOP decrease was observed in the untreated eye, indicating that very little or no systemic absorption occurred. In comparison to said reference compound, CHF 1035 exhibits a less rapid onset of action, but a longer duration of action.

Further results prove that CHF 1035 induces a persistent decrease in IOP after repeated administrations.

The 5,6-diisobutyroyloxy-2-methylamino-tetralin derivative, compared with the compound with the free catechol group at the 5,6 position or with other similar compounds (M-7), has better characteristics in terms of chemical stability and ocular bioavailability, as proved by the higher partition coefficient n-octanol/buffer pH 7.4 ($\log P_{app}$=0.75 vs. −0.9). The better chemical stability, makes the handling of the starting material easier and also allows to prepare solutions for the ophthalmic use with pH nearer to the physiological values and therefore better tolerated.

Furthermore, it has surprisingly been found that, contrary to what stated in the prior art (Järvinen T et al. Adv. Drug Deliv. Rev. 1996, 19, 203–224), the protection of the catechol group through formation of the corresponding diisobutyroyloxy derivative, besides improving corneal permeability, also increases the ocular tolerability of the drugs. The medicament is indeed well tolerated up to 5% concentration, causing neither irritation symptoms such as redness and blinking, nor other undesired side effects. Chetoni P et al. Int. J. Pharm. 105, 147–155, 1994 report that in case of, for example, albuterol, the synthesis of the corresponding esterified pro-drug, although increasing effectiveness, does not prevent its irritant effects. Dipivefrin, which has been introduced on the market as a pro-drug of adrenaline in the form of dipivaloyl ester, gives rise to side effects such as pain in the eye and in the superciliary arch as well as corneal vascularization and opacification during long-term use. (Salminen L et al. J. Ocul. Pharmacol. Ther. 11, 37–40, 1995). The in vivo use of the prodrugs of pilocarpine is associated with ocular irritation (Saarinen-Savolainen P et al. Int. J. Pharm. 133, 171–178, 1996; Suhonen P et al. Int. J. Pharm. 127, 85–94, 1996).

For its favorable characteristics, CHF 1035 can be advantageously used for the preparation of compositions for the ophthalmic use in the therapy of glaucoma. Even more preferred is the use of the corresponding (−)-(S) enantiomer which is about twice as much selective towards the α2 and $DA_2$ receptors than the racemate.

The present invention, besides CHF 1035, also includes the analogous derivative without the methyl group on the amino group. The compounds of the invention can be used in the form of salts with inorganic acids, such as hydrochloride and hydrobromide, or with organic acids such as acetate, tartrate and citrate.

The amount of active ingredient to be used will vary with the age of the patient and the severity of the glaucoma.

Generally, the concentration of the active ingredient will range from 0.001 to 5%, preferably between 0.01 and 1.0%.

For the ocular administration, the compounds can be formulated as aqueous solution or in the form of ointments, creams or gels, by using the conventional additives and excipients.

Preferred carriers for the compounds of the invention for those consisting of a sterile isotonic aqueous solution, for the administration in the form of ophthalmic drops, containing viscosity-increasing agents such as hydroxypropylmethylcelluose, stabilizing agents such as EDTA or sodium bisulfite, preservatives such as benzalkonium chloride or chlorobutanol.

Advantageously, the pH of the opthalmic composition will be adjusted between 3.0 to 7.5 by using conventional buffering agents such as borates, carbonates or phosphates. Preferably it will be adjusted between 4.0 and 5.0 avoiding buffers in order to manipulate the physiological environment of precorneal area as little as possible.

The invention is illustrated in detail by the following examples.

EXAMPLE 1

Determination of Apparent Partition Coefficient

The apparent partition coefficients ($\log P_{app}$) of CHF 1035 were determined from the distribution of the compound between 1-octanol and phosphate buffer solution (50 mM; pH 1.4, 5.5, 6.5 and 7.4). The phosphate buffer solution and 1-octanol were saturated with each other, prior to partition study, by shaking vigorously for 24 h. A known concentration of CHF 1035 in the phosphate buffer solution was shaken 60 minutes with suitable volume of saturated 1-octanol. After shaking, the phases were separated by centrifugation, and the concentrations of CHF 1035 in the buffer phase were determined by HPLC before and after partitioning. The results expressed as a mean±SD (standard deviation) are reported in Table 1.

TABLE 1

| Apparent partition coefficient ($\log P_{app}$, mean ± SD, n = 3) of CHF 1035. ||
| --- | --- |
| pH of buffer solution | Log $P_{app}$ (mean ± SD, n = 3) |
| 4.5 | 0.17 ± 0.02 |
| 5.5 | 0.17 ± 0.01 |
| 6.5 | 0.20 ± 0.08 |
| 7.4 | 0.75 ± 0.02 |

CHF 1035 is a base with pKa=9.4, so its $\log P_{app}$ value increases with increased pH. The higher apparent partition coefficient would be more favorable for ophthalmic absorption. However, an acid aqueous solution should be used as a vehicle for eyedrop administration due to the better chemical stability of CHF 1035 in such pH range. The theoretical $\log P_{app}$ of the corresponding not esterified derivative turned out to be −0.9 at pH 7.4.

EXAMPLE 2

Intraocular Pressure (IOP) Studies After Single Dose in Normotensive Rabbits

Water (pH 4.5, made isotonic with sodium chloride), was selected as vehicle for the IOP-studies. Buffer solution was not used in order to manipulate the physiological environment of precorneal area as little as possible. pH 4.5 was selected to confer a good stability to CHF 1035.

Five concentrations (0.01, 0.05, 0.2, 0.5 and 1.0% w/v) of CHF 1035 were studied. Brimonidine (0.2% w/v) was used as a positive, and vehicle (water pH 4.5) as a negative control.

The experimental animals used were normotensive Dutch Belted rabbits of either gender (n=6). A single drop (25 µl) of the test solution was instilled unilaterally into the left eye (treated eye). IOP of the rabbits (treated and untreated eyes) was measured at 1 and 0 h before, and at 0.5, 1, 2, 3, 4, 5, 6 and 7 h after topical eyedrop administration. IOP at the time of eyedrop administration (0 h) was used as a baseline value. IOP was measured using a BioRad Pneumatonometer. More detailed description of the IOP measurement procedure can be found in Pharm. Res. 14, 1738–1743, 1997 and Curr. Eye Res. 14, 791–797, 1995. All the studies were set up using a randomized crossover design. At least 72 h of wash-out time was allowed for each rabbit between dosings. The irritation caused by an instilled eyedrop were evaluated by recording the extent of eyelid closure after topical eyedrop administration.

The effects expressed as change from baseline (mmHg) are reported in Table 2 and 3 as mean±SEM (standard error of mean).

1.0%. In cases of smaller doses (i.e., doses 0.01% and 0.05%), the maximum decrease in IOP tends to be earlier. The prodrug-nature may also prolong the duration of action of CHF 1035.

Topical administration (single dose) of CHF 1035 did not cause significant eye irritation in rabbits: no eyelid closure was observed after topical administration (25 µl) of 0.5%, 0,2%, 0.05% and 0.01% CHF 1035 solution.

CHF 1035 also turned out to be more effective in decreasing IOP than brimonidine, and has longer duration of action than brimonidine.

No significant IOP changes was observed after vehicle administration: the IOP change was between −1.1 and 1.4 mmHg, and between 0.3 and 1.5 mmHg in the treated and in the untreated eye, respectively.

TABLE 2

Intraocular pressure (IOP) changes (mean mmHg ± SEM) in the treated eye of normotensive rabbits (n = 6) after unilateral administration of test solution.

| DOSE (%, w/v) | TIME (min) | | | | | | | | |
|---|---|---|---|---|---|---|---|---|---|
| | 0 | 30 | 60 | 120 | 180 | 240 | 300 | 360 | 420 |
| water* | 0.0 ± 0.0 | 0.7 ± 0.4 | −0.9 ± 0.4 | −0.3 ± 0.6 | 0.0 ± 0.6 | −0.2 ± 0.5 | 0.0 ± 0.7 | −0.4 ± 0.9 | 0.6 ± 0.9 |
| 1.0% CHF | 0.0 ± 0.0 | 1.3 ± 0.9 | 0.4 ± 1.0 | 0.1 ± 0.9 | −3.2 ± 1.8 | −4.9 ± 1.5 | −5.8 ± 1.6 | −6.6 ± 1.6 | −5.3 ± 1.5 |
| 0.5% CHF | 0.0 ± 0.0 | 1.8 ± 0.6 | 1.2 ± 0.7 | 0.1 ± 0.7 | −5.0 ± 1.2 | −5.6 ± 0.6 | −7.9 ± 0.9 | −6.9 ± 0.8 | −7.0 ± 0.8 |
| 0.2% CHF | 0.0 ± 0.0 | 0.8 ± 0.9 | −0.4 ± 1.1 | −2.1 ± 0.7 | −6.0 ± 0.9 | −6.3 ± 1.0 | −7.6 ± 1.5 | −6.9 ± 1.0 | −5.7 ± 1.1 |
| 0.05% CHF | 0.0 ± 0.0 | −0.4 ± 0.5 | −3.3 ± 0.4 | −6.5 ± 0.9 | −6.3 ± 0.9 | −6.7 ± 0.8 | −6.4 ± 0.8 | −5.5 ± 0.7 | −4.3 ± 0.5 |
| 0.01% CHF | 0.0 ± 0.0 | −1.9 ± 0.9 | −4.2 ± 1.1 | −5.3 ± 0.7 | −5.0 ± 1.0 | −4.5 ± 1.3 | −4.3 ± 0.9 | −2.6 ± 0.6 | −1.3 ± 0.8 |
| 0.2% Brim. | 0.0 ± 0.0 | −2.7 ± 0.9 | −7.8 ± 0.9 | −6.2 ± 1.4 | −3.9 ± 0.8 | −3.4 ± 0.7 | −2.4 ± 0.7 | −0.4 ± 0.6 | 0.2 ± 0.3 |

*= n equals 12(2 × 6) instead of 6
CHF = CHF 1035 HCl
Brim. = Brimonidine

TABLE 3

Intraocular pressure (IOP) changes (mean mmHg ± SEM) in the untreated eye of normotensive rabbits (n = 6) after unilateral administration of test solution.

| DOSE (%, w/v) | TIME (min) | | | | | | | | |
|---|---|---|---|---|---|---|---|---|---|
| | 0 | 30 | 60 | 120 | 180 | 240 | 300 | 360 | 420 |
| water* | 0.0 ± 0.0 | 0.3 ± 0.5 | −0.4 ± 0.3 | 0.0 ± 0.5 | −0.2 ± 0.4 | −0.4 ± 0.4 | −0.7 ± 0.7 | 0.3 ± 0.8 | 0.9 ± 0.4 |
| 1.0% CHF | 0.0 ± 0.0 | 2.2 ± 0.9 | 1.2 ± 1.2 | 1.0 ± 0.8 | −2.5 ± 1.3 | −1.8 ± 0.6 | −0.7 ± 0.8 | −0.2 ± 1.1 | −0.9 ± 1.0 |
| 0.5% CHF | 0.0 ± 0.0 | 2.9 ± 0.8 | 2.4 ± 0.7 | 1.4 ± 0.4 | 0.0 ± 0.5 | −0.2 ± 0.7 | −0.9 ± 0.4 | −0.7 ± 0.6 | −0.2 ± 0.3 |
| 0.2% CHF | 0.0 ± 0.0 | 1.0 ± 0.8 | 0.5 ± 1.2 | 0.0 ± 0.9 | −1.5 ± 1.2 | −1.6 ± 1.1 | −1.1 ± 1.1 | −0.7 ± 1.0 | 0.0 ± 0.8 |
| 0.05% CHF | 0.0 ± 0.0 | 0.0 ± 0.6 | 0.1 ± 0.7 | −1.5 ± 0.8 | −0.4 ± 1.0 | −1.0 ± 0.4 | −1.9 ± 0.9 | −0.6 ± 1.2 | 0.3 ± 0.7 |
| 0.01% CHF | 0.0 ± 0.0 | −1.0 ± 1.1 | −1.9 ± 1.2 | −1.6 ± 1.0 | −0.5 ± 0.7 | −1.4 ± 0.7 | −1.7 ± 0.4 | 0.0 ± 0.6 | 0.4 ± 0.7 |
| 0.2% Brim. | 0.0 ± 0.0 | −3.2 ± 1.2 | −8.7 ± 0.8 | −3.3 ± 1.3 | −1.7 ± 0.9 | −2.1 ± 1.0 | −0.6 ± 0.9 | 0.1 ± 0.6 | 0.0 ± 0.6 |

*= n equals 12(2 × 6) instead of 6
CHF = CHF 1035 HCl
Brim. = Brimonidine

CHF 1035 decreases significantly the IOP in the treated eye after topical administration into normotensive rabbits. However, no significant IOP decrease is observed in the untreated eye, which is considered to be a benefit. The minor IOP effects in untreated eye may mean minor systemic absorption and decreased risk for serious systemic side-effects.

CHF 1035 shows a late onset of action which may be caused by its prodrug-nature. The maximum decrease in IOP occurs between 5 and 6 h with doses between 0.2% and

EXAMPLE 3

Intraocular Pressure (IOP) Studies After Single Dose in Rabbits with Water-increased IOP A study versus placebo was carried out in 20 New-Zealand albino rabbits to evaluate the effects of CHF 1035 after single administration. Basal intraocular pressure (IOP) was measured in anaesthetized rabbits in both eyes. Each eye received two drops of physiological solution containing 5% of the drug. Control animals received only physiological solution. After one hour, the animals were administered by oral route with a total amount of 200 ml of distilled water. IOP increased within about one hour and normalized after about 3 hours. As no differences in IOP were observed between the two eyes, the respective tonometric curves were superimposed. IOP measurements were carried out by using a Goldman tonometer and were repeated one hour after the administration of water.

FIG. 1 shows the effect of CHF 1035 on rabbit intraocular pressure (IOP) after water loading. Values are expressed as mean (SE[1] 32 1.6–2.7). The total number of eyes per group is in brackets.

It can be appreciated that the animals pre-treated with CHF 1035 show an IOP value significantly lower than control animals.

[1] Standard error

EXAMPLE 4

Intraocular Pressure (IOP) Studies After Repeated Administration in Rabbits with Water-increased IOP The effectiveness of CHF 1035 after repeated administration was tested in a study versus placebo, in 20 New-Zealand albino rabbits. In order to induce a chronic increase of the IOP, each animal was intraocularly injected with 0.5 mg/day of α-chymotrypsin for five days. Starting from the first day of treatment, two drops of physiological saline containing 5% of the drug were instilled in each eye every 6 hours. The control animals only received physiological saline.

The IOP measurement was performed as described in example 1, before the injection and subsequently every day until the 10$^{th}$ day.

Figure 2:
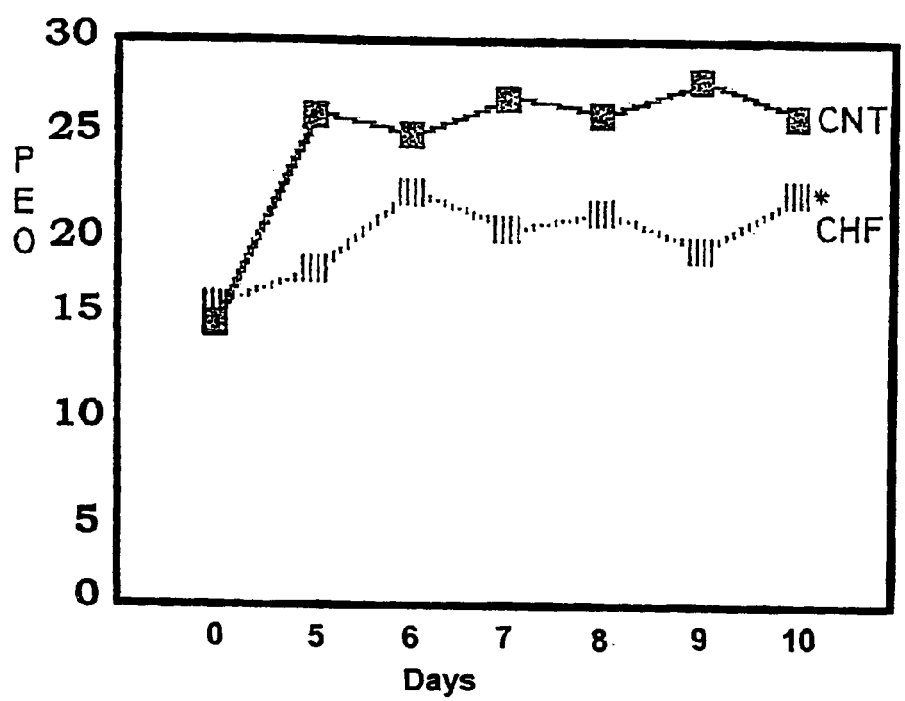

FIG. 2 reports the effect of CHF 1035 on rabbit IOP after α-chymotrypsin injection. Values are reported as mean (SE=1.2–2.6; n=20 per group).

IOP values are similar before the injection of α-chymotrypsin. However, the animals treated with CHF 1035 showed significantly lower IOP than animals treated with placebo. Moreover, the medicament turned out to be well tolerated during the whole cycle of treatment and induced no eye irritation and/or discomfort.

What is claimed is:

1. A method of treating glaucoma, comprising administering to an eye in need thereof an effective amount of at least one compound of formula I, enantiomers thereof, and salts thereof:

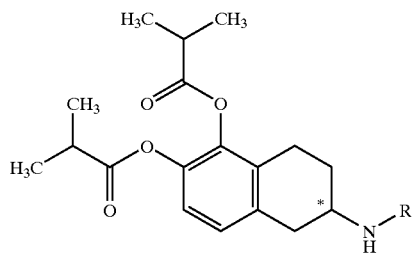

to treat the glaucoma;
wherein R is H or CH3.

2. The method of claim 1, wherein R is H.

3. The method of claim 1, wherein R is CH3.

4. The method of claim 3, wherein the compound of formula I is (–)-(S)-5,6-diisobutyroyloxy-2-methylamino-tetralin.

5. The method of claim 1, wherein the at least one compound is administered in combination with one or more suitable carriers.

6. The method of claim 1, wherein the at least one compound is formulated as an aqueous solution.

7. The method of claim 6, wherein the at least one compound is present in a concentration of from 0.001 to 5%.

8. The method of claim 6, wherein the at least one compound is present in a concentration of from 0.01 to 1%.

9. The method of claim 1, wherein the at least one compound is formulated as an ointment.

10. The method of claim 9, wherein the at least one compound is present in a concentration of from 0.001 to 5%.

11. The method of claim 9, wherein the at least one compound is present in a concentration of from 0.01 to 1%.

12. The method of claim 1, wherein the at least one compound is formulated as a cream.

13. The method of claim 12, wherein the at least one compound is present in a concentration of from 0.001 to 5%.

14. The method of claim 12, wherein the at least one compound is present in a concentration of from 0.01 to 1%.

15. The method of claim 1, wherein the at least one compound is formulated gel.

16. The method of claim 15, wherein the at least one compound is present in a concentration of from 0.001 to 5%.

17. The method of claim 15, wherein the at least one compound is present in a concentration of from 0.01 to 1%.

* * * * *